United States Patent
Iskandar et al.

(10) Patent No.: US 10,709,879 B2
(45) Date of Patent: Jul. 14, 2020

(54) CEREBROSPINAL-FLUID SHUNT VALVE SYSTEM

(71) Applicant: Wisconsin Alumni Research Foundation, Madison, WI (US)

(72) Inventors: Bermans J. Iskandar, Madison, WI (US); Joshua Medow, Verona, WI (US); Christopher Luzzio, Madison, WI (US); John G. Webster, Madison, WI (US); Mehdi Shokoueinejad Maragheh, Madison, WI (US); Fa Wang, Madison, WI (US); Xuan Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 502 days.

(21) Appl. No.: 15/473,126

(22) Filed: Mar. 29, 2017

(65) Prior Publication Data
US 2018/0280670 A1  Oct. 4, 2018

(51) Int. Cl.
*A61M 27/00* (2006.01)
(52) U.S. Cl.
CPC ... *A61M 27/006* (2013.01); *A61M 2202/0464* (2013.01); *A61M 2205/3331* (2013.01); *A61M 2210/0693* (2013.01)
(58) Field of Classification Search
CPC .................................................. A61M 27/006
See application file for complete search history.

(56) References Cited

U.S. PATENT DOCUMENTS

| | | | | |
|---|---|---|---|---|
| 6,024,340 A | * | 2/2000 | Lazarus | F16K 31/004 251/129.06 |
| 6,248,080 B1 | * | 6/2001 | Miesel | A61B 5/0215 600/311 |
| 7,951,105 B2 | | 5/2011 | Medow et al. | |
| 8,876,744 B2 | | 11/2014 | Hsu et al. | |
| 2011/0301575 A1 | * | 12/2011 | Miesel | A61M 5/14276 604/891.1 |
| 2012/0302938 A1 | * | 11/2012 | Browd | A61M 27/006 604/9 |
| 2012/0316492 A1 | * | 12/2012 | Chappel | A61M 5/16881 604/67 |

OTHER PUBLICATIONS

Barry R. Lutz et al. "New and improved ways to treat hydrocephalus: Pursuit of a smart shunt." Surgical neurology international 4 (published online Mar. 19, 2013): pp. S38-S50. US.

* cited by examiner

*Primary Examiner* — Benjamin J Klein
(74) *Attorney, Agent, or Firm* — Boyle Fredrickson S.C.

(57) ABSTRACT

The present invention provides a cerebrospinal fluid shunt system that monitors the intracranial pressures over a portion of a monitoring cycle to calculate short intervals of drainage for every monitoring cycle necessary to produce the desired pressure correction. The system operates to significantly reduce the time during which draining occurs allowing tissue surrounding the catheter to rebound from the catheter holes returning to its normal position for a sufficient amount of time to recover its normal shape.

29 Claims, 7 Drawing Sheets

CEREBROSPINAL-FLUID SHUNT VALVE SYSTEM

CROSS REFERENCE TO RELATED APPLICATIONS

--

STATEMENT REGARDING FEDERALLY SPONSORED RESEARCH OR DEVELOPMENT

--

BACKGROUND OF THE INVENTION

The present invention relates to neurosurgical devices used for treating hydrocephalus and, more specifically, to ventriculoperitoneal (VP) shunts that relieve pressure on the brain caused by excess fluid accumulation within the brain.

Hydrocephalus is a condition caused by an abnormal accumulation of cerebrospinal fluid (CSF) within the ventricles of the brain. Cerebrospinal fluid is produced in the choroid plexuses of the ventricles of the brain and circulates through the ventricular system of the brain to the subarachnoid spaces in the cranium and spine to be absorbed into the bloodstream. The fluid is used to surround the brain and spinal cord and acts as a protective cushion or buffer against injury. It also contains nutrients and proteins for nourishment and functioning of the brain while clearing away waste products.

Hydrocephalus occurs when there is an imbalance between the amount of CSF that is produced and the amount that is absorbed. When CSF builds up within the brain, it causes the ventricles to enlarge and increases the pressure inside the skull.

Hydrocephalus is typically treated through the surgical placement of a shunt system within the brain. The shunt system places a drainage tube between the brain's ventricles or the subarachnoid space and another body region, typically the abdominal cavity (or pleural cavity, heart atrium, and others), where the CSF can be absorbed. This creates an alternative route for removal of CSF buildup within the brain. Valves may be positioned within the shunt pathway to regulate flow based upon differential pressure, i.e., the pressure difference at the proximal catheter tip and the pressure at the drainage end.

Shunt failure is a very common complication requiring immediate shunt revision (the replacement or reprogramming of the pre-existing shunt). A shunt malfunction that does not receive immediate medical attention can be life-threatening or result in permanent neurologic injury. The shunt failure rate is relatively high (in the pediatric population, the shunt failure rate after one year is 40-50% and after five years is at nearly 100%) and it is not uncommon for patients to have multiple shunt revisions within their lifetime.

A leading cause of shunt failure is partial or complete blockage of the shunt. Both the proximal catheter placed in the brain and the distal catheter that provides the draining may become blocked. Typically when there is a blockage, the shunt must be replaced.

Under-drainage due to shunt blockage can cause the ventricles to increase in size and fail to remedy the symptoms of hydrocephalus. However, over-drainage is also undesired since it decreases the size of the ventricles and creates slit like ventricles. Over-drainage has also been found to increase the likelihood of shunt blockages.

SUMMARY OF THE INVENTION

While the inventors do not wish to be bound by a particular theory, there is now evidence that blockage of the shunt may be caused by the continuous over-draining of CSF to relieve CSF buildup, even at low levels. Over time the ability of the tissue to rebound diminishes causing the tissue to be permanently deformed and lodged within the catheter holes. Tissue entering the catheter can tear or break off and create blockages within the catheter over time.

The present invention operates to significantly reduce the time during which draining occurs allowing tissue surrounding the catheter to rebound from the catheter holes returning to its normal position for a sufficient amount of time to recover its normal shape. Intracranial pressure (ICP) is the differential pressure between ICP and ambient pressure. Ambient pressure may be measured by an ambient pressure sensor in an external reader or implanted. Instead of allowing CSF to drain at a nearly constant flow rate, the present invention monitors the ICP over a portion of a monitoring cycle to calculate short intervals of drainage for every monitoring, cycle necessary to produce the desired, pressure correction. By continuously alternating between valve fully open and valve fully closed, the system can allow the brain tissue to retain its normal shape with reduced blockage.

Specifically, in one embodiment, the invention provides a cerebral shunt used to treat an abnormal accumulation of cerebrospinal fluid (CSF) in a brain of a patient, comprising: a catheter implanted within the brain of the patient with a proximal portion within the brain opposite a distal portion diverting CSF out of the brain to another region of the patient; a pressure sensor implanted within the brain of the patient and producing a signal representing an ICP; a valve that permits excess CSF to drain out of the brain through the catheter in an open position and prevents the excess CSF from passing out of the brain through the catheter in a closed position; and a valve driver receiving the signal representing the ICP controlling the valve to switch the valve between the open position and closed position in a cycle for successive cycles so that the relative time that the valve is in the open position versus the closed position is a function of ICP.

It is thus a feature of at least one embodiment of the invention to electrically control operation of the valve according to measured ICP to permit sophisticated control of the valve operation that can minimize long periods of drainage such as can cause tissue distortion.

The valve driver may be adapted to open the valve during each cycle for a period of time that is less time than a period of time that the valve is closed. The valve driver may be adapted to open the valve less than 10% of the time over each cycle. The valve driver may be adapted to open the valve less than 2% of the time over each cycle.

It is thus a feature of at least one embodiment of the invention to increase the time during which the valve is in a closed position to minimize tissue deformation.

The valve driver may be adapted to open the valve for a continuous period of time. The continuous period of time may be less than 5 seconds. The valve may be open for a period of time limited to a predetermined time permitting tissue surrounding the valve to be released from, the valve without irreversible shape change.

It is thus a feature of at least one embodiment of the invention to permit the tissue to recover between drainage sessions, preventing permanent deformation.

A controller may receive the signal from the pressure sensor over a period of time and averaging, the signal over the period of time. The period of time may be between 2 and 10 minutes.

It is thus a feature of at least one embodiment of the invention to provide continuous monitoring without the need for continuous drainage.

The valve driver may operate to attenuate an effect of sudden changes in the signal representing the ICP.

It is thus a feature of at least one embodiment of the invention to prevent sudden pressure changes or spikes (for example, caused by patient movement, sneezing, coughing) to cause over-drainage.

The pressure sensor may provide a pair of opposed conductive plates at least one plate flexing in response to ICP enabling circuitry detecting flexure according to at least one of varying resonant frequency, capacitance and piezo-resistance.

It is thus a feature of at least one embodiment of the invention to monitor an absolute pressure change to discount gravitational effects which influence pressure difference valves.

A biocompatible holder may comprise a disk having a broad face supporting an elongated tube extending downwardly therefrom and supporting the pressure sensor on a distal end of the tube.

It is thus a feature of at least one embodiment of the invention to allow for implantation of the pressure sensor to a desired depth within the skull while communicating with pressure sensor electronics outside of the skull.

The valve comprises a piezo bender actuator receiving electrical signals from the valve controller to be electrically actuated to reposition the piezo bender actuator to open or close the valve.

It is thus a feature of at least one embodiment of the invention to utilize piezoelectric qualities of materials in creating simplified electrically actuated valves.

The piezo bender actuator may be a cantilever repositioning to change a position of a collar extending around a tube having an orifice in series with the catheter to block the orifice. The piezo bender may be a cantilever repositioning to change a position of a plug removably insertable within an orifice of the catheter wherein the orifice permits CSF to drain.

It is thus a feature of at least one embodiment of the invention to utilize simple on-off valves.

A wireless transmitter may communicate the signal to an external wireless reader. The wireless transmitter may be an RFID device or other suitable wireless communication method.

It is thus a feature of at least one embodiment of the invention to permit external communication and control with the pressure sensing and valve control systems.

The present invention also provides a method of treating hydrocephalus where there is an abnormal accumulation of cerebrospinal fluid (CSF) in a brain of a patient comprising the steps of providing a cerebral shunt comprising a catheter having a proximal portion opposite a distal portion; a pressure sensor producing a signal representing an ICP; a valve limiting flow through the catheter between an open and closed position; implanting the proximal portion of the catheter within the brain of the patient and the distal portion outside the brain of the patient; implanting the sensor within the brain of the patient; and receiving, the signal representing the ICP controlling the valve to switch the valve between the open position and closed position in a cycle for successive cycles so that the relative time that the valve is in the open position versus the closed position is a function of ICP.

These particular objects and advantages may apply to only some embodiments falling within the claims and thus do not define the scope of the invention.

DETAILED DESCRIPTION OF THE PREFERRED EMBODIMENT

Figure 1:
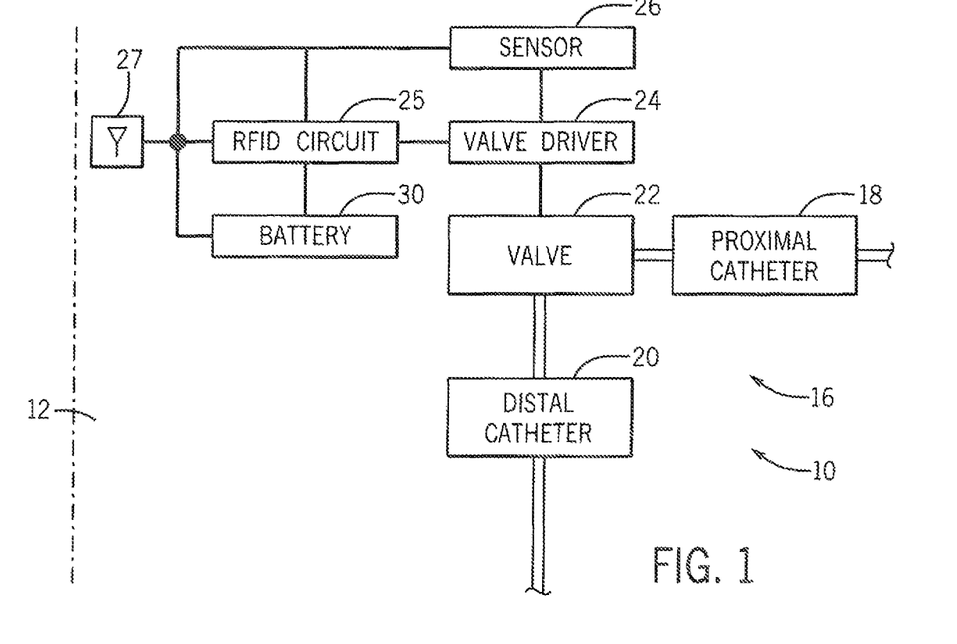
FIG. 1 is a schematic of a cerebral shunt system of one embodiment of the present invention showing with a pressure sensor system installed within a patient.
Figure 12:
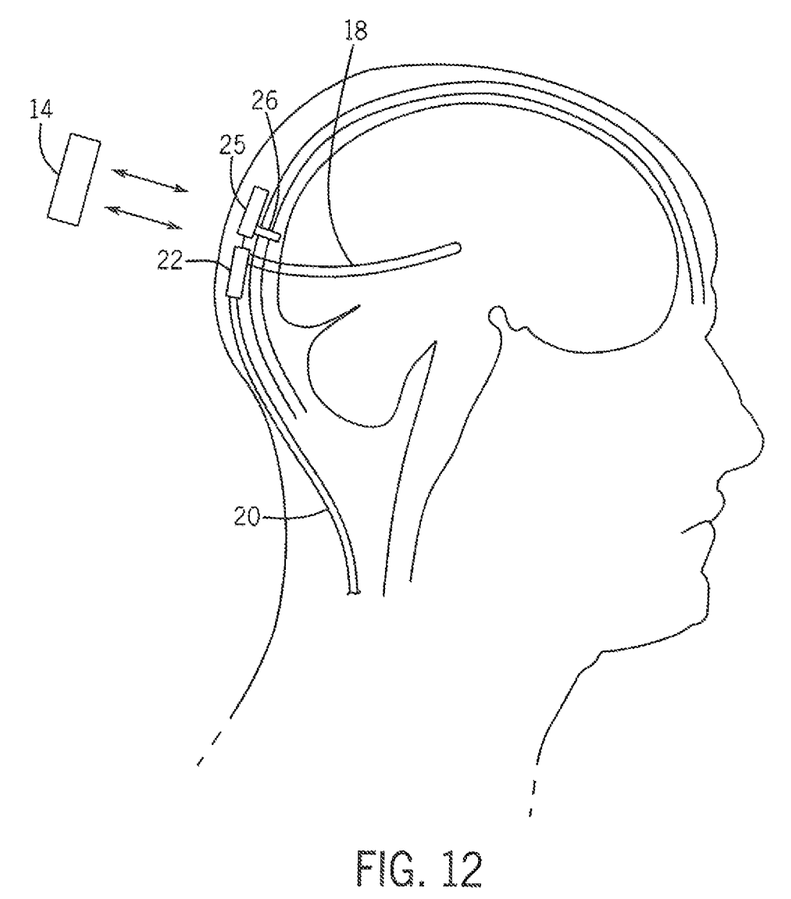
FIG. 12 is a simplified depiction of the cerebral shunt system installed within a skull of a patient.

Referring now to FIGS. 1 and 12, a cerebral shunt system 10 of the present invention may be partially implanted within a human patient 12. The cerebral shunt system 10 may include embedded devices 16 installed beneath the scalp and/or skull 13 of the human patient 12 communicating with an external reader or telemeter device 14 to be discussed below.

The embedded devices 16 assist with drainage of excess cerebrospinal fluid (CSF) surrounding the brain of the patient 12. The CSF may be drained from within the brain to another location within the patient's body, such as the abdominal cavity, peritoneal cavity, pleural cavity, or heart, able to absorb the excess CSF.

The embedded devices 16 include a proximal catheter 18 that may be surgically implanted in the cranium or spine to approach the ventricle or other CSF space where CSF resides so that CSF may be drained from the patient's brain or spinal canal. The proximal catheter 18 may be closed at the tip but include a number of small drainage holes, approximately 1 mm in diameter, running along a length of the proximal catheter 18. The holes may be arranged in rows and are generally positioned at a distal end of the catheter allowing the CSF to flow from the ventricles or subarachnoid space through the holes and into the proximal catheter 18. The CSF is drained from the brain's ventricles or the subarachnoid space by flowing through the proximal catheter 18 leading away from the brain. The proximal catheter 18 extends from the brain through a small hole in the skull 13 to the outside of the skull 13.

A distal catheter 20 fluidly communicates with the proximal catheter 18 and typically runs underneath the scalp of the patient 12 and to a drainage site such as the abdominal cavity, peritoneal cavity, pleural, cavity, or heart. The distal catheter 20 may have a closed tip and also contain a number of small drainage holes, approximately 1 mm in diameter, running along a length of the distal catheter 20. The holes may be arranged in rows and are mostly positioned at a distal drainage end of the catheter allowing the CSF to drain out of the distal catheter 20 into the drainage site. The catheter may be open ended with or without slits.

A valve 22 is located between the proximal catheter 18 and the distal catheter 20, facilitating the fluid communication therebetween and regulating the flow rate of CSF through the catheter system. In one embodiment of the present invention, the valve 22 may be installed outside the skull 13 of the patient 12 but underneath the skin of the patient 12 and coupling the proximal catheter 18 to the distal catheter 20. It is understood that the valve 22 may be positioned anywhere along the catheter system to regulate flow rate in a similar manner. For example, the valve 22 may be located at the proximal catheter 18, distal catheter 20, or anywhere between the two catheters.

Operation of the valve 22 may be controlled by a valve driver 24 in the form of a microcontroller providing an electrical drive signal to the valve 22 according to a valve control program 132. The valve control program 132 may be processed by a valve driver 24 determining whether the valve 22 should be open or closed according to a sensed ICP. The valve driver 24 may include a digital processor, electronic memory holding the valve control program 132, an electrical interface circuit for communicating between the valve driver 24 and other devices as is generally understood in the art. According to the valve control program 132, the valve driver 24 will send a signal to the valve 22 to open or close the valve 22 thus allowing CSF to flow out of the skull 13 of the patient 12 or not flow out of the skull 13 of the patient 12. For example, when the valve 22 is open, CSF may drain through the distal catheter 20 whereas when the valve 22 is closed, CSF is not drained through the distal catheter 20.

The ICP may be determined by a pressure sensor 26 (to be described in more detail below) implanted within the skull 13 of the patient 12, e.g., in the brain parenchyma. The pressure sensor 26 may sense an absolute ICP, or condition representative of pressure, and deliver that sensed signal to the valve driver 24.

The valve driver/microcontroller 24 may also communicate with an RFID circuit 25 (or other wireless communication method) providing two-way communication through an antenna 27 with a handheld telemeter device 14. The antenna 27 may also communicate with a battery system 30 providing power to the other elements of the embedded devices 16 using standard wireless power transmission techniques such as radio-frequency identification (RFID) and resonance based inductive coupling technology.

As noted above, and referring to FIG. 2, the cerebral shunt system 10 may also include an external reader such as a handheld telemeter device 14 that may be positioned outside the patient's skull 13 to receive ICP data from the pressure sensor 26 and to program the valve control program 132 as well as to provide electrical charging current for batteries 30 communicating with the pressure sensor 26 and the valve driver 24.

Figure 2:
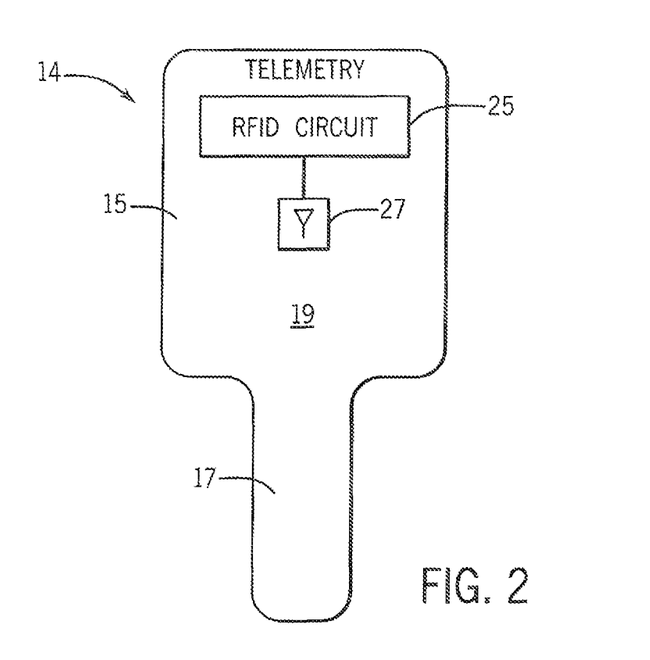
FIG. 2 is an external telemeter device wirelessly communicating with the pressure sensor system within the patient.

In one embodiment, the telemeter device 14 may be a handheld wand having a base 15 attached to a handle 17 for gripping, where in use, the base 15 has a broad face 19 positioned in close proximity to the patient's skull 13 so that the telemeter device 14 may wirelessly communicate with the embedded devices 16 within the patient 12. The telemeter device 14, e.g., within the base 15 portion, may contain an antenna 27 to facilitate the wireless communication therebetween. In one embodiment, telemeter device 14 may make use of a standard RFID circuit 25 (or other wireless communication device) for communicating with the RFID circuit 25 (or other wireless communication device) of the embedded devices 16 such as may communicate with the valve driver 24.

The telemeter device 14 may connect to a computer (e.g., PC or laptop) through an electrical conductor, such as a USB cable. Physicians may control the cerebral shunt system 10 on a Graphical User Interface (GUI) of the computer to set parameters or thresholds for the valve, as will be further discussed below.

It is understood that the telemeter device 14 may communicate with the embedded devices 16 through a wired or wireless connection and instead of being an external device, the telemeter device 14 may also be implanted or embedded device within the patient 12.

Sensing System

Figures 3A, 3B, 4, 5:
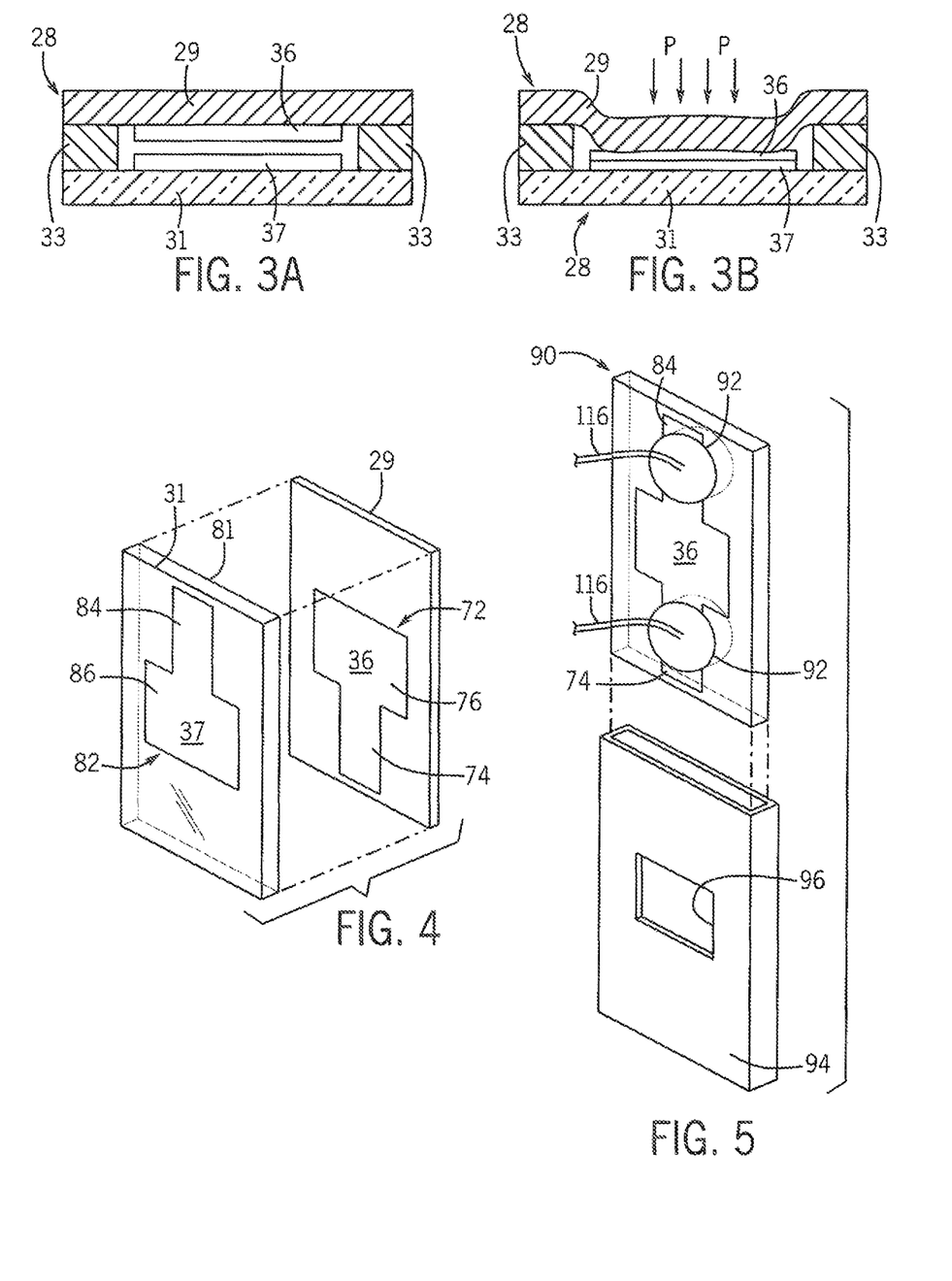
FIG. 3A is a side elevation view of a pressure sensor system having upper and lower spiral metal coils/plates spaced apart in parallel alignment
FIG. 3B is the side elevation view of the pressure sensor system of FIG. 3A and showing a pressure applied to the top plate causing deflection of the upper metal coil/plate.
FIG. 4 is an exploded view of the pressure sensor having a first deflecting plate and a second non-moveable plate.
FIG. 5 is an exploded view of the plates of FIG. 4 bonded together and inserted within a protective sleeve and exposing the silicon membrane.

Referring now to FIGS. 3A and 3B, the pressure sensor 26 may include a housing 28 having a deformable upper plate 29 opposite and substantially parallel to a non-deformable lower plate 31. The upper plate 29 and lower plate 31 are held in separation by standoffs 33 extending at the outer edges between the two plates which seal between the upper plate 29 and lower plate 31 at a predetermined pressure for example atmospheric pressure or vacuum. The lower surface of the upper plate 29 and upper surface of the lower plate 31 support two oppositely disposed metal electrodes 36, 37 in parallel separation to each other. The metal electrodes 36, 37 may be made of copper, silver gold, or a material which may elastically deform with deformation of the upper plate 29.

When pressure (P) is applied to the upper plate 29 due to increased ICP caused by CSF buildup, the upper metal electrode 36 (center diaphragm) bends toward the lower metal electrode 37. In response to the physical repositioning of the upper metal electrode 36 with respect to the lower metal electrode 37, the capacitance between the upper metal electrode 36 and lower metal electrode 37 changes. This variation may be detected by a capacitive sensing routine executed by the valve driver 24 for example such as measures a change of charging time of the capacitance or a change in frequency when the capacitance is made part of a tuned resonant circuit.

The change in capacitance for small deflections may be proportional or otherwise functionally related to the applied ICP on the center diaphragm thus an ICP can be calculated.

Referring now to FIG. 4, in one embodiment of the pressure sensor 26 the upper plate 29 may be made of a thin silicon membrane. The first plate 29 contains a T-shaped well 72 extending within the upper plate 29 for supporting a similarly shaped diaphragm or metal electrode 36 that deforms under pressure. The T-shaped well 72, and correspondingly the metal electrode 36, has a vertical channel or stem 74 of the T extending downward from a middle of the upper plate 29 toward a bottom of the upper plate 29 and a horizontal arm 76 extending across the top of the stem 74 forming the top of the T. The horizontal arm 76 is rectangular and is substantially centered within the upper plate 29 to define a center diaphragm. The metal electrode 36 fits within the T shaped well 72 and has a substantially identical shape as the T-shaped well 72 and fitting therein so as to fully encompass the T-shaped well 72.

The non-deformable lower plate 31 may be a thick glass plate providing a "ground plane" that does not deform under ICP. A front side 81 of the plate 31 supports an electrode 37 in a similar manner as the upper plate 29. The second plate 31 may contain an upside down T-shaped well 82 supporting the electrode 37 but not necessarily extending all the way through the glass plate but just at a surface. The T-shaped well 82, and correspondingly the electrode 37, has a vertical channel or stem 84 of the T extending upward from a middle of the plate toward a top of the second plate 31 and a horizontal arm 86 extending across the bottom of the stem 84 at the bottom of the upside down T. The horizontal arm 86 is rectangular and substantially centered within the second plate 31 to correspond in relative position with the horizontal arm 76 of the first plate 29. The T-shaped well 82 carries the T-shaped electrode 37 having a substantially similar shape as the T-shaped well 82 and fitting therein so as to fully encompass the T-shaped well 82.

Referring now to FIG. 5, the plate 29 is bonded to the front side 81 of the second plate 31 to create a bonded plate 90. When the first plate 70 and second plate 31 are bonded together, the plates 29 and 31 are aligned such that the horizontal arms 76, 86 of the first plate 29 and second plate 31 overlap and align such that the center diaphragms of the metal electrodes 36 and 37 are positioned in substantially parallel separation to create what is known as a parallel plate capacitor arrangement. The metal plates 29, 31 may be separated by a vacuum to prevent electric transfer between the plates.

As shown, in the bonded plate 90, holes 92 may be drilled through the bonded plate 90 within the vertical stem 74 of the T of the first plate 29 and vertical stem 84 of the T of the second plate 31 respectively so that each metal plate 36 and 37 may be electrically communicated with through wires 116.

The bonded plate 90 may be covered by a protective sleeve such as parylene or silastic 94 having a front, back, and side walls corresponding with the walls of the bonded plate 90 and slid over the bonded plate 90 to provide a protective layer to the bonded plate 90. The sleeve 94 includes a rectangular opening 96 allowing the horizontal arm 76 (center diaphragm) of the first plate 70 to be exposed to an applied ICP.

ICP (P) may be applied to the metal diaphragm through the rectangular opening silicon membrane 96 of the sleeve 94 causing the metal plate 36 to deflect while the electrode 37 remains non-movable within the glass plate 31. The deflection of the metal plate 29 varies a distance between the two metal plates 36 and 37 changing the capacitance when a voltage is applied. The voltage may be applied to the plates through wires 116 attached to the holes 92 allowing electricity to flow from the wires 116 to the conductive plates and allowing a capacitance to be recorded. Detection of the capacitance is proportional to the applied ICP on the center diaphragm thus an ICP may be calculated.

Figure 6:
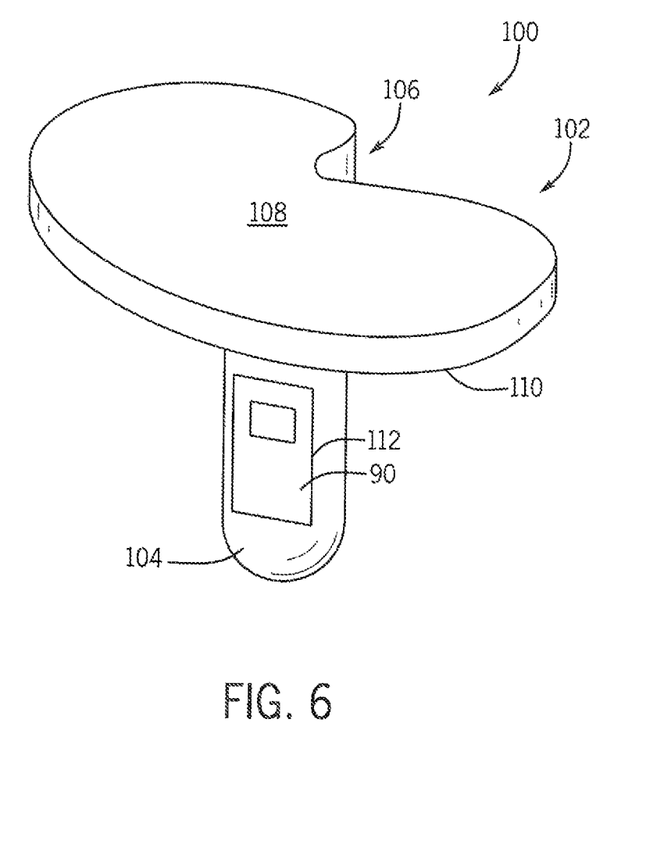
FIG. 6 is the bonded plates of FIG. 5 installed within a biocompatible holder.

Referring to FIG. 6, the bonded plate 90 held within the sleeve 94 may be carried by a biocompatible holder 100 that is installed within the skull of the patient 12 to measure ICP changes. The biocompatible holder 100 may include a disk 102 supporting a downwardly extending tube 104.

The disk 102 may be circular in shape and flattened to provide a top surface 108 opposite a bottom surface 110 to fit a human skull shape. A perimeter of the disk 102 may include a U-shaped cutout 106.

A tube 104 extends downwardly from the bottom surface 110 of the disk 102 providing an oblong support structure with a rounded tip for carrying the pressure sensor 26, for example, the bonded plate 90. The tube 104 may have a rectangular receiving socket 112 within an outer surface of the tube 104 for receiving the pressure sensor 26. The receiving socket 112 may be sized to receive the pressure sensor 26 therein and may include fastening or bonding means to secure the pressure sensor 26 in place. The pressure sensor 26 is installed within the receiving socket 112 such that the center diaphragm of the pressure sensor 26 is exposed allowing ICP pressure to be applied thereon.

The electrical wires 116 coupled to the pressure sensor 26, for example, to each plate 29, 31 of the bonded plate 90, may run from a distal end of the tube 104, through the tube 104, and to the disk 102 where the electrical components are held so as to communicate an electrical signal and a capacitance measurement. The electrical wires 116 may communicate with the valve microcontroller 24, RFID circuit 25 (or other wireless communication device), and other electronics for transmission to and from the implanted or external RFID circuit 25 (or other wireless communication device).

In an alternative embodiment, it will be understood that the capacitance formed by the electrical plates 36 and 37 may be incorporated into an electrically resonant circuit that may be interrogated remotely, for example using wireless signals from the telemeter device 14 which by measuring the frequency of this circuit (in the manner of a grid dip meter) can determine the ICP. Thus the pressure sensor 26 may be used independently as an ICP sensor or may communicate with the valve controller 24 wirelessly. The resonant circuit may be formed in part by shaping the electrical plates 36 and 37 into, spiral coils acting both as antennas and inductors for the purpose of creating the resonant circuit. In this case the pressure sensor 26 does not need to be wired or powered by an external power source, instead relying upon an external reader to detect and respond to physical changes within the pressure sensor 26.

In an alternative embodiment, the pressure sensor 26 may be a commercially available piezoresistive sensor, e.g., where a silicon diaphragm is exposed to the ICP. A silicon diaphragm is used in which an ICP pressure difference across the diaphragm leads to a change of resistivity which may be measured by the valve controller 24. For example, the piezoresistive sensor may be Amphenol P330 series or All Sensors DS-0287 series, both of which are commercially available.

It is understood that the pressure sensor 26 may be biocompatible and MRI compatible and may be used in conjunction with a holder 100 that is also biocompatible and MRI compatible. The RFID (or other wireless communication device) circuit 25 and antenna 27 may by isolated by a magnetic switch or reed switch that when in the presence of a magnetic field, such as when within an MRI machine, the antenna 27 will disable. The magnetic switch opens the circuit in high magnetic fields in each orthogonal plane. This prevents overheating and overcharging of the system in magnetic environments. Alternatively, various voltage threshold circuit such as back to back diodes or the like may be used to shunt the antenna 27 for example by detuning it.

Valve Control System

Figure 7:
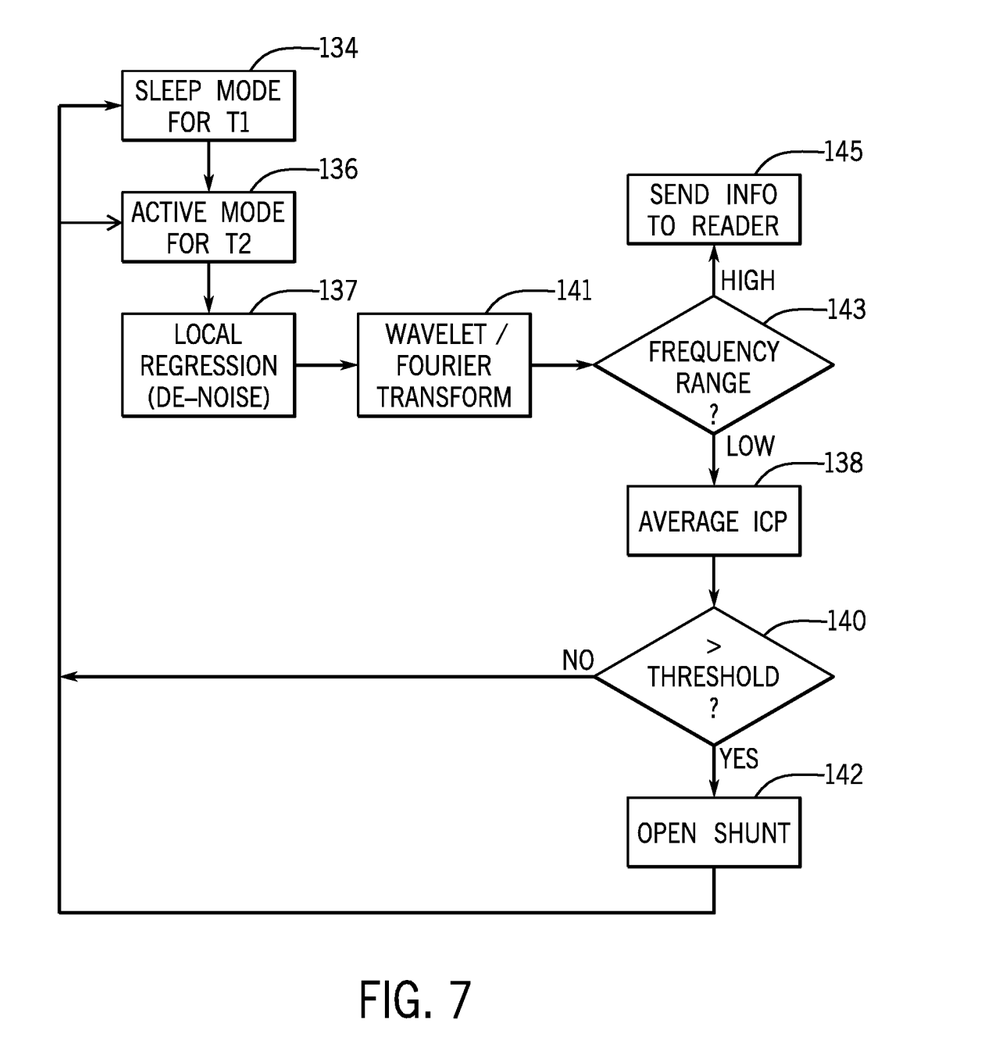
FIG. 7 is a flow diagram of a valve control system.
Figure 8:
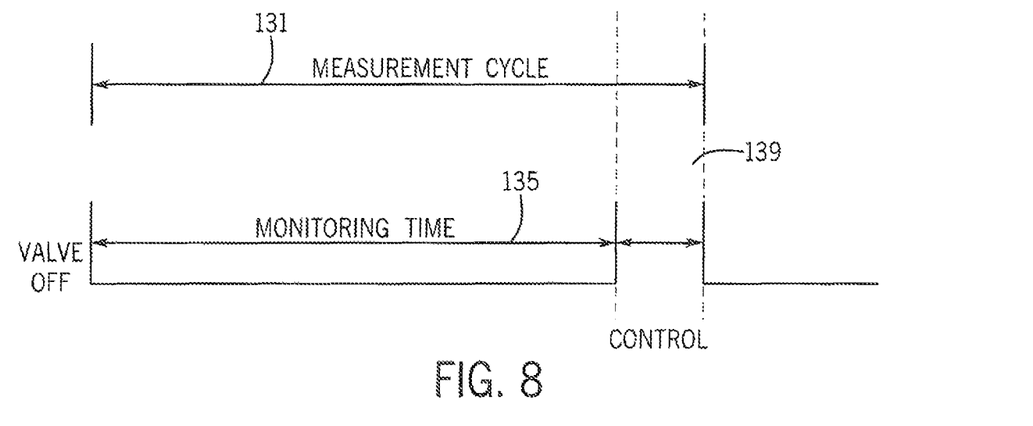
FIG. 8 is a graph showing the measurement cycle of the valve control system over time.

Referring now to FIGS. 7 and 8, the valve driver 24 executing the valve control program 132, may receive the electrical signal indicating an ICP measurement of the pressure sensor 26 wirelessly or through a wired connection. The ICP measurement may consists of pulse waveforms having up to five peaks for a single pulse. The first three peaks (P1, P2, P3) generally determine the main, waveform called a "P wave". P1 is due to the arterial pulse, P2 is due to cerebral compliance, and P3 is due to closure of the aortic valve, which causes the dicrotic notch.

The valve microcontroller 24 operates a program 132 comprising a number of steps to be described. The program may operate a "sleep mode" whereby the control program 132 does not record the incoming ICP sensor signals as indicated by the process step 134. The sleep mode helps to conserve energy consumption and, battery life.

After a predetermined amount of time (T1) has passed or when a predetermined condition occurs, such as when the patient 12 moves or during certain times of the day, the program proceeds to an "active mode" during which the control program 132 executes a measurement cycle 131 during which it records the incoming ICP sensor signals during a monitoring time 135 (T2) to determine an ICP over a predetermined time period as indicated by the process step 136. For example the active mode may record the incoming ICP sensor signals during a monitoring time 135 (T2). In one embodiment, the monitoring time 135 may be for a five or ten minute period or a period between five and ten minutes.

During or after the monitoring time 135 (T2) has passed, the recorded data is, processed using de-noising and smoothing algorithms and techniques, for example, moving average, low pass filter, exponential smoothing, etc. In one embodiment, the algorithm is a local regression method as indicated by the process step 137. In one embodiment, the local regression algorithm assigns regression weights to the value within a dynamic range with a length chosen to be 5:

$$w_i = \left(1 - \left|\frac{x - x_i}{d(x)}\right|^3\right)^3$$

where x is the predicted value associated with the original signal data to be smoothed, $x_i$ is the neighbor of x in the dynamic range, and d(x) is half of the dynamic range length at the x-axis. Based on these weights, the weighted linear least-squares regression is performed. The regression uses a second degree polynomial.

It is understood that other filtering techniques, e.g., moving average, low pass filter, exponential smoothing, etc., may be applied to the recorded data to remove outlier data and/or noise. For example, the filtering techniques may be used to attenuate or remove spikes within the incoming ICP sensor signals, for example, when the patient 12 stands up or coughs.

After the signal de-noising step, a wavelet transform will be applied to the signal to get the frequency range of the signal as indicated by process step 141. The process then proceeds to process step 143 where the frequency range of the resulting signal is determined.

If the frequency range is a high frequency range, the signal information is outputted to the medical professional for further evaluation as indicated by process step 145. For example, the high frequency may indicate a critical patient condition or system failure that requires human intervention. If the frequency range is a low frequency range (e.g., DC level), then the shunt will be controlled depending on the signal and proceed to averaging step 138.

As indicated by process step 138, when the frequency range is in the low frequency range, the filtered recorded data is averaged over the recording time period.

The averaged ICP is compared against a threshold value (TH) which may be set by the operator (for example, 12 mm Hg). If an average ICP pressure value is over the threshold value, it is considered "high" and requires CSF draining and if an average ICP pressure value is under the threshold value is considered "normal" or "low" and does not require CSF draining as indicated by process step 140. If the averaged ICP is above the threshold value, the process continues to step 142 to open the valve 22 for a short control time 139 (T3) depending on the amount of difference between the averaged ICP and the threshold value, allowing the CSF to drain for the short period of time and then re-closing the valve immediately after. In one embodiment, the control time 139 may be between two and five seconds. This functional relationship between the error between the averaged ICP and the threshold value may use a known control algorithm such as proportional/integral/derivative algorithms for stability. The process then loops back to sleep mode 134 or active mode 136. If the averaged ICP is within a predetermined acceptability zone of the threshold pressure, the process automatically loops back to sleep mode 134 or active mode 136 with the valve 22 remaining closed. If the process loops back to active mode, the incoming electrical signals are recorded for the next predetermined time period and the cycle is repeated. If the process loops back to sleep mode 134, the process remains dormant until the program proceeds to active mode.

The operator may determine the parameters (TH, T1, T2, T3) associated with the control program 132. These parameters may be, conveyed to the valve microcontroller 24 through the telemeter devise 14 or may be preprogrammed into the device. For example the operator may determine when and how long the control system remains in sleep mode 134. The operator may also determine when the system proceeds to active mode 136. The operator may also determine the threshold value (step 140) and the amount of time the valve 22 is opened (step 142).

In an alternative embodiment of the present invention, instead of exceeding a pressure threshold level, the valve may open based upon a pressure elevation over time. For example, the pressure elevation may be determined by an accelerometer or altimeter used to measure changes in altitude, vertical velocities, or altitudes of the device above a fixed level. In this respect, the valve may open as a function of intracranial pressure elevation and time. The valve may close as a function of a lower intracranial pressure parameter.

A cycle may be defined as switching from a closed valve 22 to an open valve 22 for successive cycles. It is understood that the valve 22 remains closed for the majority of time of the cycle whereas the valve 22 is opened for only short periods of time within the cycle when a high ICP is detected. In one embodiment, the valve may be opened 2 to 3 seconds or less than five seconds. In this respect, drainage of the CSF occurs for only short periods of time, minimizing the possibility of over drainage and allowing the tissue surrounding the catheter to rebound from a deformed position within the holes of the catheter when the valve 22 is off (i.e., tissue recovery period). The valve 22 may be opened for a period of time limited to a predetermined time permitting tissue surrounding the catheter to be release from the catheter without irreversible shape change. In one embodiment, the valve 22 may remain open for less than 25% of the cycle time or less than 10% of the cycle time or less than 2% of the cycle time.

Although the closed valve 22 may indicate zero flow, it may also mean low flow allowing the tissue to be released form the catheter. In this respect, the open valve 22 may indicate a flow rate that substantially holds the tissue in the holes of the catheter.

Electrically Actuated Valves

Figure 9:
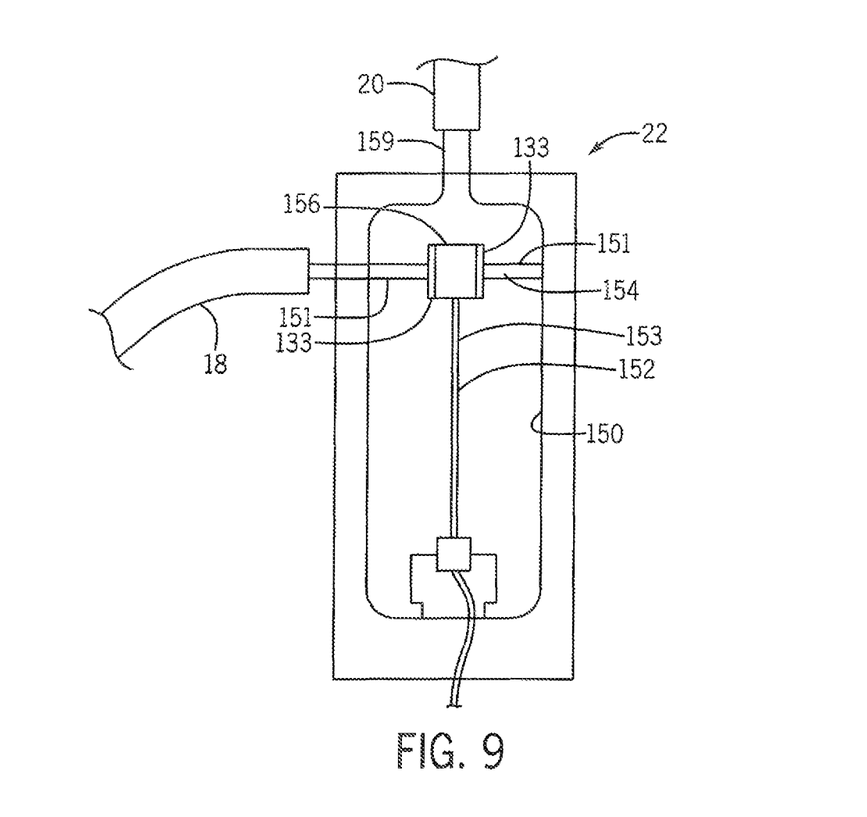
FIG. 9 is a valve of one embodiment of the present invention installed within a housing.
Figure 10:
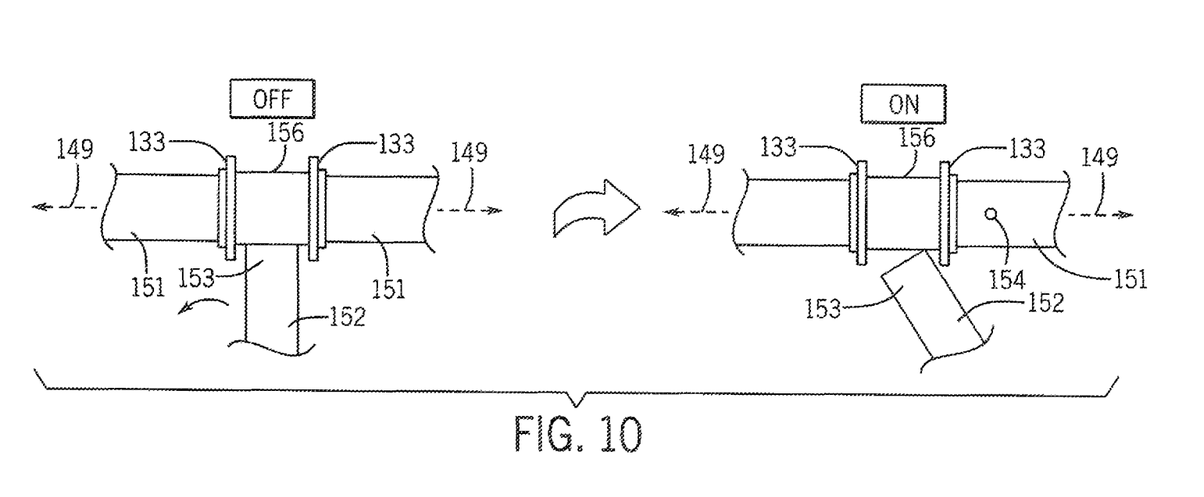
FIG. 10 is an enlarged schematic of the valve of FIG. 9 showing a cantilevered piezo bender actuator sliding a collar to block or expose a tubular orifice permitting CSF flow into the housing.
Figure 11:
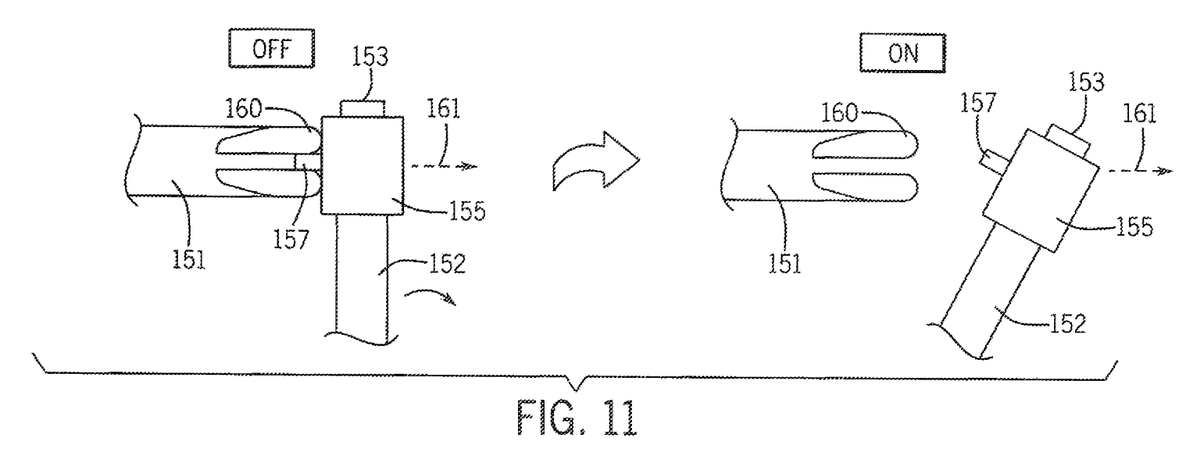
FIG. 11 is a schematic of a valve of an alternative embodiment of the present invention showing a cantilevered piezo bender actuator having a plug to block or expose a tubular orifice permitting CSF flow into the housing.

Referring now to FIGS. 9, 10 and 11 the valve, microcontroller 24 may receive a signal from the pressure sensor 26, through a wired or wireless communication, indicating an ICP signal. The valve microcontroller 24 then runs the valve control program 132 to determine whether the valve should be on or off. The on-off instruction is then sent to the valve driver 24 to regulate the valve 22 of the cerebral shunt system 10 between an on and off state.

In one embodiment of the present invention, the electrical signal causes a piezo bender actuator 152 to bend between a first position and a second position, opening and closing the valve 22. The piezo bender actuator 152 may be a cantilevered finger having at least one piezoelectric layer of material permitting the finger to displace in at least one direction, for example, providing 1 to 2 mm displacement. The piezo bender actuator 152 may be made of a ceramic, crystal, composite material, or known piezoelectric material and include side surface, electrodes attached to electrical wires 116 that may communicate with the valve driver 24.

Referring specifically to FIGS. 9 and 10, the valve's on and off state may be actuated by an electrical signal delivered from the valve driver 24 to the valve 22 to electrically actuate the valve 22.

The valve 22 may provide for an enclosed chamber 150 (as shown in FIG. 9) communicating with the proximal catheter 18. An inflow tube 151 spans the enclosed chamber 150 and passes through one wall of the chamber 150 to the distal catheter 20. The proximal catheter 18 may be connected in series with the inflow tube 151 regulating CSF flow to a drain tube 159 connected in series to the distal catheter 20. The transverse inflow tube 151 and drain tube 159 may be constructed of stainless steel and, may have a diameter less than the catheter 18, 20 allowing the catheter 18, 20 to couple to the tubes 151, 159 by sliding thereover.

As seen best in FIG. 10, the inflow tube 151 has a small orifice 154 normally covered by a blocking collar 156 that prevents flow between the proximal catheter 18 and distal catheter 20 (for example, prevents flow from the orifice 154 into the chamber 150 and to the drain tube 159).

A piezo electric bender 152 is fixed within the chamber 150 and extends in cantilevered fashion between bender guides 133 which allow the piezo electric bender 152 to slide the collar 156 along the inflow tube 151 in order to open and close the orifice 154. The piezo bender actuator 152 extends toward the transverse inflow tube 151 and is displaced in one direction along axis 149 when a voltage is applied and in an opposite direction along axis 149 when a second voltage is applied.

When the piezo bender actuator 152 is in a first closed position, the collar 156 is in a position whereby the collar 156 covers the orifice 154 preventing CSF to drain from the inflow tube 151. When the piezo bender actuator 152 is in a second open position, the collar 156 is in a position whereby an orifice 154 of the transverse inflow tube 151 is exposed allowing CSF to drain from the transverse inflow tube 151. It is understood that various gaskets or other sealing means may be used to prevent leakage.

Referring now to FIG. 11, in an alternative embodiment of the present invention, the valve 22 may receive CSF from the proximal catheter 18 through an inflow tube 151 in a similar manner. The valve 22 may control flow from the inflow tube 151 to a drain tube 159 in series with the distal catheter 20 permitting CSF to drain.

The valve 22 may provide a housing with a chamber (FIG. 9) supporting the inflow tube 151 and having an orifice 154 extending along an axis 161 used to drain CSF to the drain tube 159. The housing may support a piezo bender actuator 152 defined by a cantilevered finger supported at one end and unrestricted on the opposite end 153 to become displaced in one direction substantially along axis 161 when a voltage is applied and in the opposite direction substantially along axis 161 when a second voltage is applied.

The free end 153 of the piezo bender actuator 152 may include a polymer gasket material 155 wrapped around the free end 153 and also including a flexible pin 157 extending from the gasket material 155 toward the orifice 154 substantially along axis 161 when displaced. The flexible pin 157 is sized and positioned to fit within the orifice 154 so as to plug the orifice 154 preventing the flow of CSF therethrough.

When the piezo bender actuator 152 is in a first closed position, the free end 153 is positioned toward the orifice 160 and the pin 157 is plugged within the orifice 160 preventing CSF to drain from the inflow tube 151. When the piezo bender actuator 152 is in a second open position, the free end 153 is positioned away from the orifice 160 and the orifice 160 is unblocked allowing CSF to drain from the inflow tube 151.

It is understood that many types of electrically actuated valves 22 may be used in conjunction with the present invention for regulating the flow rate of CSF out of the brain and into a drainage site. While the valve 22 is generally described as an on-off valve it is understood that the valve 22 may also regulate the flow rate (varied flow rate above 0) when in the on position.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference, which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context. When elements are indicated to be electrically connected, that connection may be direct or through an intervening conductive element.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A cerebral shunt used to treat an abnormal accumulation of cerebrospinal fluid (CSF) in a brain of a patient, comprising:
   a catheter adapted for implantation within the brain of the patient with a proximal portion within the brain opposite a distal portion diverting CSF out of the brain to another region of the patient;
   a pressure sensor adapted for implantation within the brain of the patient and to produce a signal representing an intracranial pressure;
   a valve connected to the catheter to conduct excess CSF to drain out of the brain through the catheter in an open position and to prevent the excess CSF from passing out of the brain through the catheter in a closed position; and
   a valve driver control circuit communicating with the pressure sensor and the valve and operating to receive the signal representing the intracranial pressure and to control the valve to switch the valve between the open position and closed position in a cycle for successive cycles according to the signal representing the intracranial pressure and providing a measure of intracranial pressure so that the valve is opened at a first time when the measure of intracranial pressure is above a threshold value and the valve is closed at a second time following the first time while the measure of intracranial pressure still remains above the threshold value and to repeat an opening and closing of the valve while the measure of intracranial pressure remains above the threshold value;
   wherein the valve comprises a piezo bender actuator receiving electrical signals from the valve controller to be electrically actuated to reposition the piezo bender actuator to open or close the valve; and
   wherein the piezo bender actuator is a cantilever repositionable to change a position of a collar extending around a tube having an orifice in series with the catheter to block the orifice.

2. The cerebral shunt of claim 1 wherein the valve driver is adapted to open the valve during each cycle for a period of time that is less time than a period of time that the valve is closed.

3. The cerebral shunt of claim 2 wherein the valve driver is adapted to open the valve less than 10% of a total period of time of each cycle.

4. The cerebral shunt of claim 3 wherein the valve driver is adapted to open the valve less than 2% of a total period of time of each cycle.

5. The cerebral shunt of claim 2 wherein the valve driver is adapted to open the valve for a continuous period of less than 5 seconds.

6. The cerebral shunt of claim 1 wherein the valve driver is adapted to open the valve for a period of time limited to a predetermined time permitting tissue surrounding the catheter to be released from the catheter without irreversible shape change.

7. The cerebral shunt of claim 1 wherein the valve driver control circuit is a controller receiving the signal from the pressure sensor over a period of time and averaging the signal over the period of time.

8. The cerebral shunt of claim 7 wherein the valve driver operates to attenuate an effect of sudden changes in the signal representing the intracranial pressure.

9. The cerebral shunt of claim 7 wherein the valve driver is adapted to receive a signal from an ambient pressure sensor in an external reader.

10. The cerebral shunt of claim 9 wherein the external reader is adapted to receive user defined valve parameters and send the valve parameters wirelessly to the valve driver.

11. The cerebral shunt of claim 7 wherein the period of time is between 5 and 10 minutes.

12. The cerebral shunt of claim 1 wherein the pressure sensor provides a pair of opposed conductive plates, at least one plate flexing in response to intracranial pressure circuitry detecting flexure according to at least one of varying resonant frequency, capacitance and piezo-resistance.

13. The cerebral shunt of claim 1 further comprising a biocompatible holder comprising a disk having a broad face supporting an elongated tube extending downwardly therefrom and supporting the pressure sensor on a distal end of the tube.

14. The cerebral shunt of claim 1 further comprising a wireless transmitter adapted to communicate the signal to an external wireless reader.

15. The cerebral shunt of claim 14 wherein the wireless transmitter is a RFID device.

16. The cerebral shunt of claim 1 wherein the valve is adapted to open as a function of intracranial pressure elevation and time, and the valve is adapted to close based on a low intracranial pressure user defined parameter.

17. The cerebral shunt of claim 1 wherein the valve driver is adapted to open the valve during each cycle for a period of time that is a function of the measure of intracranial pressure.

18. A cerebral shunt used to treat an abnormal accumulation of cerebrospinal fluid (CSF) in a brain of a patient, comprising:
   a catheter adapted for implantation within the brain of the patient with a proximal portion within the brain opposite a distal portion diverting CSF out of the brain to another region of the patient;
   a pressure sensor adapted for implantation within the brain of the patient and to produce a signal representing an intracranial pressure;
   a valve connected to the catheter to conduct excess CSF to drain out of the brain through the catheter in an open position and to prevent the excess CSF from passing out of the brain through the catheter in a closed position; and
   a valve driver control circuit communicating with the pressure sensor and the valve and operating to receive the signal representing the intracranial pressure and to control the valve to switch the valve between the open position and closed position in a cycle for successive cycles according to the signal representing the intracranial pressure and providing a measure of intracranial pressure so that the valve is opened at a first time when the measure of intracranial pressure is above a threshold value and the valve is closed at a second time following the first time while the measure of intracranial pressure still remains above the threshold value and to repeat an opening and closing of the valve while the measure of intracranial pressure remains above the threshold value;

wherein the valve comprises a piezo bender actuator receiving electrical signals from the valve controller to be electrically actuated to reposition the piezo bender actuator to open or close the valve; and wherein the piezo bender is a cantilever repositionable to change a position of a plug removably insertable within an orifice of the catheter wherein the orifice permits CSF to drain.

19. The cerebral shunt of claim 18 wherein the valve driver is adapted to open the valve during each cycle for a period of time that is less time than a period of time that the valve is closed.

20. The cerebral shunt of claim 19 wherein the valve driver is adapted to open the valve less than 10% of a total period of time of each cycle.

21. The cerebral shunt of claim 20 wherein the valve driver is adapted to open the valve less than 2% of a total period of time of each cycle.

22. The cerebral shunt of claim 19 wherein the valve driver is adapted to open the valve for a continuous period of less than 5 seconds.

23. The cerebral shunt of claim 18 wherein the valve driver is adapted to open the valve for a period of time limited to a predetermined time permitting tissue surrounding the catheter to be released from the catheter without irreversible shape change.

24. The cerebral shunt of claim 18 wherein the valve driver control circuit is a controller receiving the signal from the pressure sensor over a period of time and averaging the signal over the period of time.

25. The cerebral shunt of claim 18 wherein the valve driver is adapted to open the valve during each cycle for a period of time that is a function of the measure of intracranial pressure.

26. A method of treating hydrocephalus where there is an abnormal accumulation of cerebrospinal fluid (CSF) in a brain of a patient comprising the steps of:

providing a cerebral shunt comprising a catheter having a proximal portion opposite a distal portion;

a pressure sensor producing a signal representing an intracranial pressure;

a valve limiting flow through the catheter between an open and closed position;

implanting the proximal portion of the catheter within the brain of the patient and the distal portion outside the brain of the patient;

implanting the pressure sensor within the brain of the patient; and receiving the signal representing the intracranial pressure to control the valve to switch the valve between the open position and closed position in a cycle for successive cycles according to the signal representing the intracranial pressure and providing a measure of intracranial pressure so that the valve is opened at a first time when the measure of intracranial pressure is above a threshold value and the valve is closed at a second time following the first time while the measure of intracranial pressure still remains above the threshold value and to repeat an opening and closing of the valve while the measure of intracranial pressure remains above the threshold value wherein the valve comprises a piezo bender actuator receiving electrical signals from the valve controller to be electrically actuated to reposition the piezo bender actuator to open or close the valve; and wherein the piezo bender actuator is a cantilever repositionable to change a position of (i) a collar extending around a tube having an orifice in series with the catheter to block the orifice or (ii) a plug removably insertable within an orifice of the catheter wherein the orifice permits CSF to drain.

27. The method of claim 26 further comprising the step of opening the valve during each cycle for a period of time that is less time than a period of time that the valve is closed.

28. The method of claim 26 further comprising the step of receiving the signal from the pressure sensor over a period of time and averaging the signal over the period of time.

29. The method of claim 26 wherein the catheter is in the ventricular or spinal compartment and drains to the abdomen or other body space.

* * * * *